(12) United States Patent
Shaw

(10) Patent No.: US 9,017,396 B2
(45) Date of Patent: Apr. 28, 2015

(54) PROSTHETIC VALVES FOR MEDICAL APPLICATION

(76) Inventor: David Peter Shaw, Christchurch (NZ)

( * ) Notice: Subject to any disclaimer, the term of this patent is extended or adjusted under 35 U.S.C. 154(b) by 322 days.

(21) Appl. No.: 10/563,387

(22) PCT Filed: Jul. 9, 2004

(86) PCT No.: PCT/NZ2004/000146
§ 371 (c)(1),
(2), (4) Date: Jan. 5, 2006

(87) PCT Pub. No.: WO2005/007017
PCT Pub. Date: Jan. 27, 2005

(65) Prior Publication Data
US 2006/0161250 A1  Jul. 20, 2006

(30) Foreign Application Priority Data

Jul. 16, 2003 (NZ) .......................... 527025

(51) Int. Cl.
*A61F 2/06* (2013.01)
*A61F 2/24* (2006.01)

(52) U.S. Cl.
CPC ............. *A61F 2/2412* (2013.01); *A61F 2/2403* (2013.01); *A61F 2/2475* (2013.01)

(58) Field of Classification Search
CPC ........... A61F 2210/0004; A61F 2/2412; A61F 2/2418; A61F 2002/075; A61F 2002/826; A61F 2/07; A61F 2/24; A61F 2/2427; A61F 2/2475
USPC .......................... 63/2.11–2.42; 623/2.11–2.42
See application file for complete search history.

(56) References Cited

U.S. PATENT DOCUMENTS

| | | | |
|---|---|---|---|
| 3,717,883 A | 2/1973 | Mosher | |
| 3,906,549 A | 9/1975 | Bucalo | |
| 4,759,758 A | 7/1988 | Gabbay | |
| 6,592,619 B2 | 7/2003 | Melvin | |
| 6,869,444 B2 * | 3/2005 | Gabbay | 623/2.36 |
| 7,267,686 B2 * | 9/2007 | DiMatteo et al. | 623/1.24 |
| 7,335,218 B2 * | 2/2008 | Wilson et al. | 606/185 |
| 2002/0123802 A1 | 9/2002 | Snyders | 623/2.18 |
| 2002/0138138 A1 * | 9/2002 | Yang | 623/2.18 |
| 2003/0023303 A1 * | 1/2003 | Palmaz et al. | 623/2.18 |
| 2005/0070995 A1 * | 3/2005 | Zilla et al. | 623/1.32 |

FOREIGN PATENT DOCUMENTS

| | | | | |
|---|---|---|---|---|
| EP | 0183904 A2 | 6/1986 | | |
| EP | 0 331 345 A2 * | 2/1989 | | A61F 2/24 |

(Continued)

OTHER PUBLICATIONS

Mikolich, Brandon M., et al., "MRI Assessment of the Efffects of a Nitinol Mesh Wrap, etc.", Abstract, 1 Page (Jul. 24, 2003).

(Continued)

*Primary Examiner* — David Isabella
*Assistant Examiner* — Ann Schillinger
(74) *Attorney, Agent, or Firm* — Galbreath Law Offices, P.C.; John A. Galbreath

(57) ABSTRACT

A prosthetic valve in the form of a flap valve which includes one or more flaps arranged to allow movement of liquid through the valve only in one direction, in which the or each flap is made of a flexible open work structure of a medically acceptable metal such as titanium or a titanium alloy.

24 Claims, 7 Drawing Sheets

(56) References Cited

FOREIGN PATENT DOCUMENTS

| | | | | |
|---|---|---|---|---|
| FR | 2682284 | 10/1991 | ................ | A61F 2/12 |
| GB | 1145816 | 10/1967 | ................ | A61F 1/22 |
| JP | 2000513248 A | 10/2000 | | |
| JP | 2001500033 A | 1/2001 | | |
| JP | 2005505343 A | 2/2005 | | |
| WO | WO 82/02829 | 9/1982 | ................ | A61F 1/22 |
| WO | WO9629957 | 10/1996 | | |
| WO | WO 99/15224 A | 4/1999 | | |
| WO | WO 02/24119 A1 | 3/2002 | | |
| WO | WO 02/41764 A2 | 5/2002 | | |
| WO | WO0247575 A2 | 6/2002 | | |
| WO | WO03003943 A2 | 1/2003 | | |
| WO | WO03013337 A2 | 2/2003 | | |

OTHER PUBLICATIONS

Webpage Printout, http://www.pyramed.co.uk/products_gastroenterology.html; *Pyramed Gastroenterology Products*; Medical Device Suppliers, 2 pp. (Jul. 26, 2004).

Webpage Printout, http://www.sma-inc.com/html/vascular_stents.html; *Johnson Marthey, Nickel Titanium*, "Woven Niti Wires", 1 Page (Jul. 26, 2004).

Webpage Printout, http://www.atticacom.co.uk/micrometals/special_wires.html; *Micro-Metals*, "Special Wires", 1 Page (Jul. 26, 2004).

Webpage Printout, http://www.discoverchemistry.com/dev2-docroot/student/real_world/materials/metals; Real-World Chemistry Materials, "Metals" 6 pp. (Jul. 26, 2004.

Webpage Printout, http://www.med.nus.edu.sg/paed/medical_education/cardiac?thumbnail/; *Patent Ductus Arteriosus (PDA)* "Preterm Ductus", 4 pp. (Jul. 26, 2004).

Webpage printout, http://heart.bmijournals.com/cgi/content/full/82/5/644; *Heart Online*; "Transcatheter Closure of Atrial Septal Defects", 4 pp.; (Jul. 26, 2004).

Gries, Thomas (Prof. Dr.); Slide Presentation; "ITA—Partner in Medical Technologies; Latest Developments in Medical Textile Products", ITA Institut für Textiltechnik; 17 pp. (undated).

Larousse Dictionary of Science and Technology, 1995; 2 pages, Larousse Kingfisher Chambers Inc., NY, NY.

\* cited by examiner

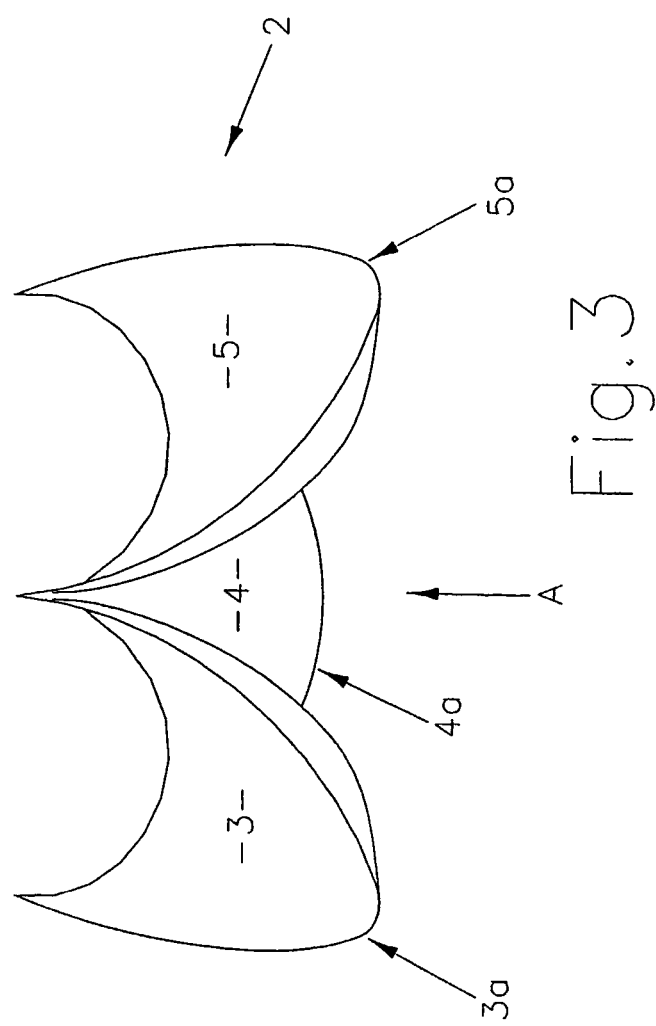

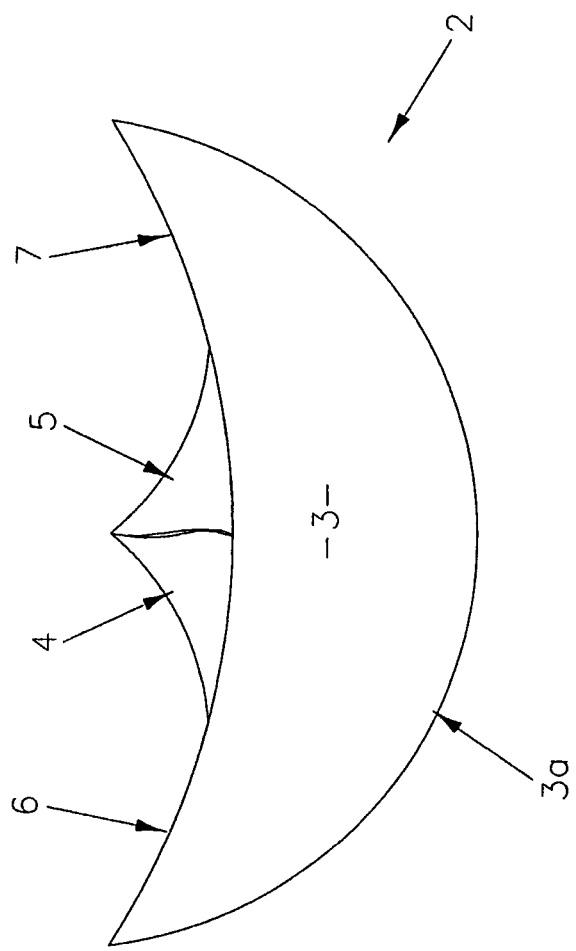

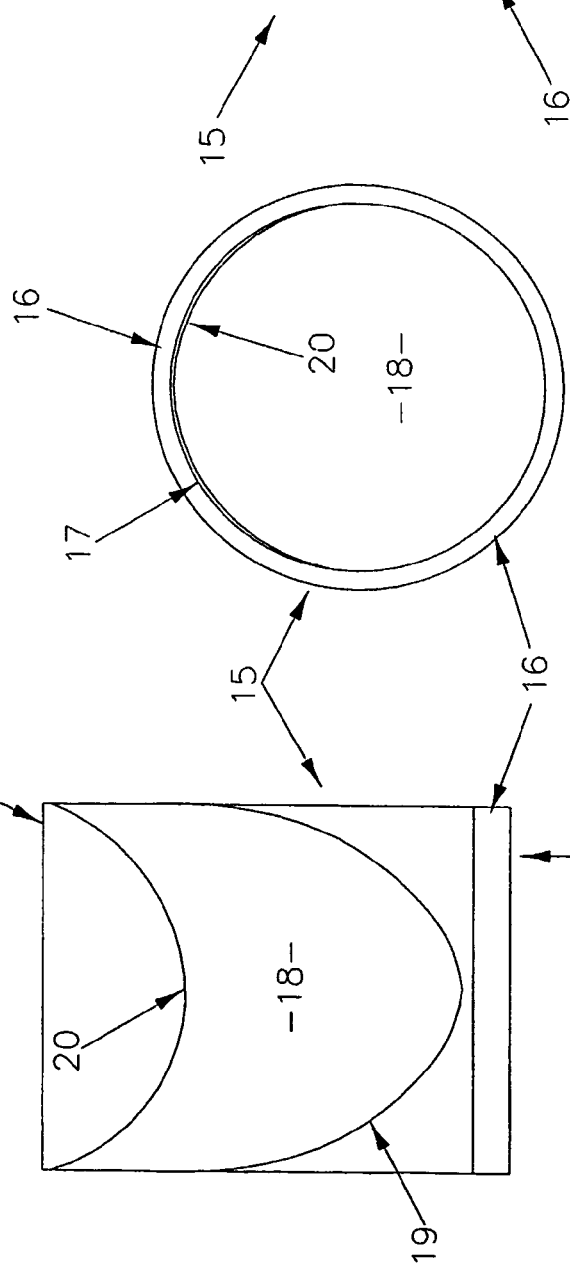

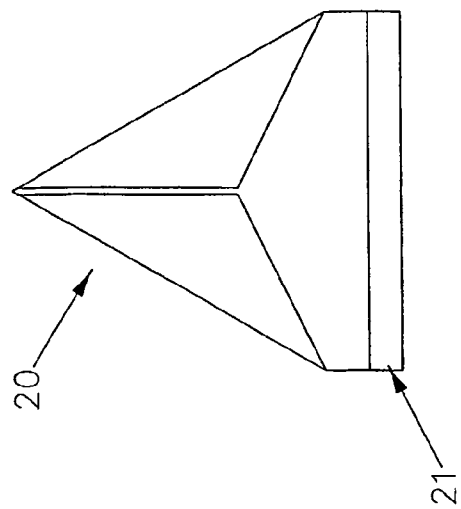
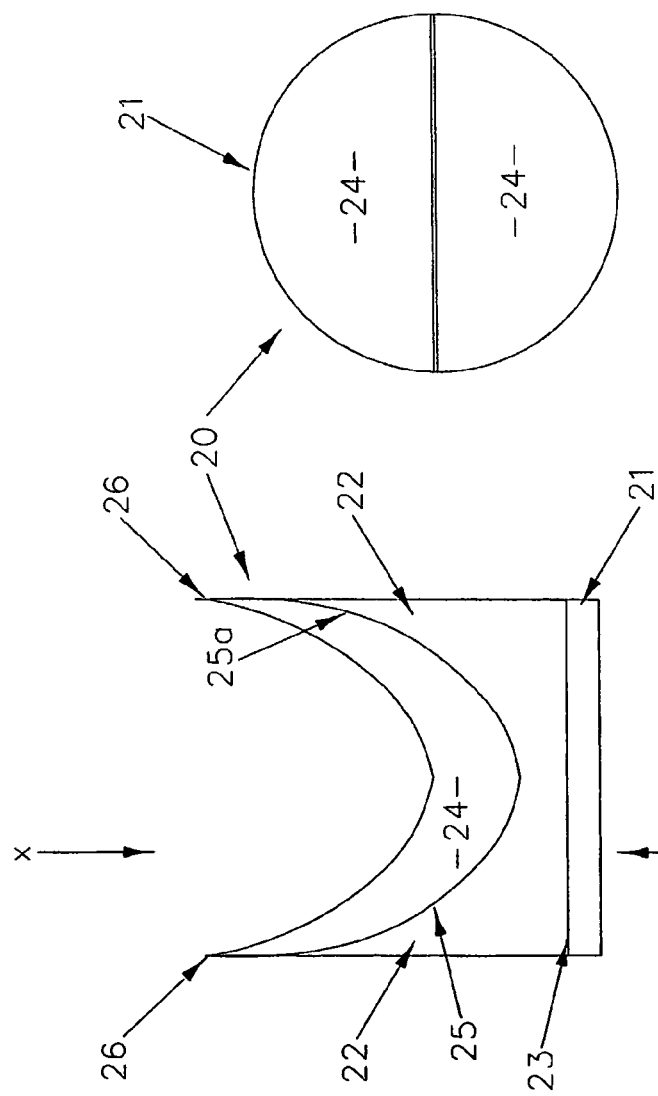
Fig.6c
Fig.6b
Fig.6a

PROSTHETIC VALVES FOR MEDICAL APPLICATION

CROSS REFERENCE TO RELATED APPLICATION

This application is a 35 U.S.C. §371 of and claims priority to PCT International Application Number PCT/NZ2004/000146, which was filed 9 Jul. 2004 (9 Jul. 2004), and was published in English, which was based on New Zealand Patent Application No. 527025 which was filed 16 Jul. 2003 (16 Jul. 2003) and the teachings of which are incorporated herein by reference.

TECHNICAL FIELD

The present invention relates to prosthetic valves for medical application. The valve of the present invention has been developed with special reference to a prosthetic heart valve, and therefore will be described with particular reference to this application. However, it will be appreciated that the valve of the present invention also could be used in other medical applications (e.g. as a venous valve).

BACKGROUND ART

Prosthetic heart valves are used to replace a patient's own defective or damaged valves. Prosthetic heart valves currently in use are divided into two broad categories:—tissue valves and mechanical valves.

Tissue valves are either naturally-formed valves taken from pig hearts or valves formed from pericardium tissue taken from bovine hearts. In general, tissue valves are well accepted by the patient's body and require only the minimum anticoagulation treatment. However, tissue valves have the drawback that they wear out relatively rapidly, with a life of between 10 and 20 years.

Mechanical valves have excellent durability:—accelerated testing suggests that mechanical valves may have a life of the order of 200 years. However, mechanical valves have the drawback that they are not readily accepted by a patient's body and require long-term anticoagulation treatment to prevent thromboembolic complications. This is undesirable from the point of view of the patient's general health.

It is therefore an object of the present invention to provide a prosthetic valve, more particularly a heart valve, which has the durability of a mechanical valve but which is as compatible with the patient's body as a tissue valve, and thus requires no, or minimal, anticoagulation therapy.

DISCLOSURE OF INVENTION

The present invention provides a prosthetic valve in the form of a flap valve which includes at least one flap arranged to allow movement of liquid through the valve only in one direction, the or each flap being made of a flexible openwork structure of a medically acceptable metal.

The valve may include only a single flap, which is arranged to close against a supporting wall, or two, three, or more flaps arranged to close against each other.

The flexible open work structure may be fabricated in any of a number of different ways, e.g. a knitted structure, a woven structure, a chainmail type of structure, or a thin flexible perforated plate.

Preferred materials are titanium or a medically approved titanium alloy such as the titanium/nickel alloy Nitenol™. To be used for the knitted, woven, chainmail type of structures, the metal used must be capable of being drawn as a fine wire.

The valves with two or more flaps may be stented or stentless.

BRIEF DESCRIPTION OF DRAWINGS

By way of example only, a preferred embodiment of the present invention is described in detail, with reference to the accompanying drawings in which:—

FIG. 3 is a side view taken along the line of Arrow III of the valve of FIG. 1;

FIG. 4 is a side view taken along the line of Arrow IV of the valve of FIG. 1;

FIGS. 5 *a,b* and *c*, are respectively side, plan and cross-sectional views of a unicuspid and valve in accordance with the present invention;

FIGS. 6*a, b* and *c*, are respectively side, plan and cross-sectional views of a bicuspid valve in accordance with the present invention.

BEST MODE FOR CARRYING OUT THE INVENTION

Figure 1:
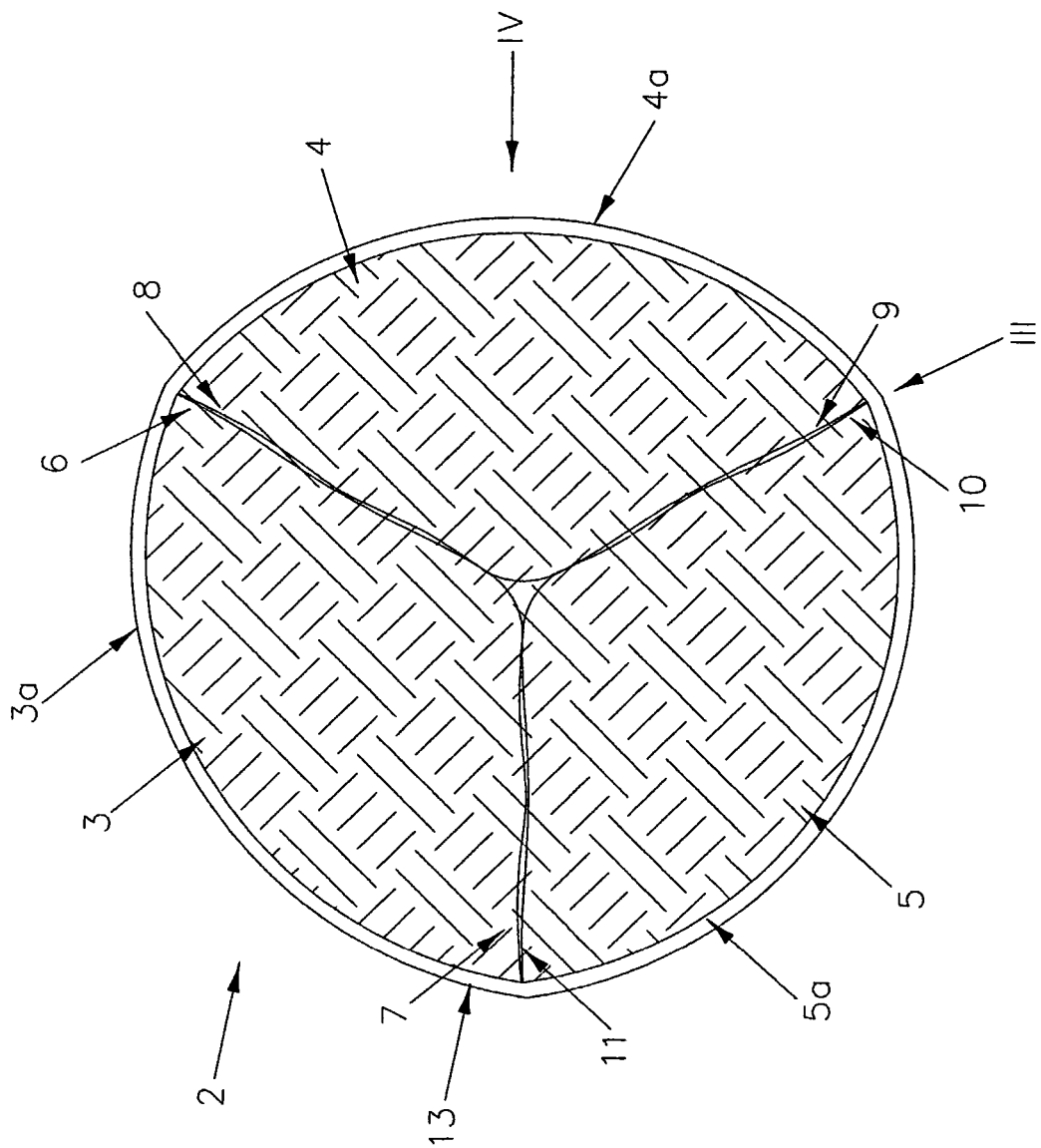
FIG. 1 is a plan view of a tricuspid prosthetic heart valve in accordance with the present invention.
Figure 2:
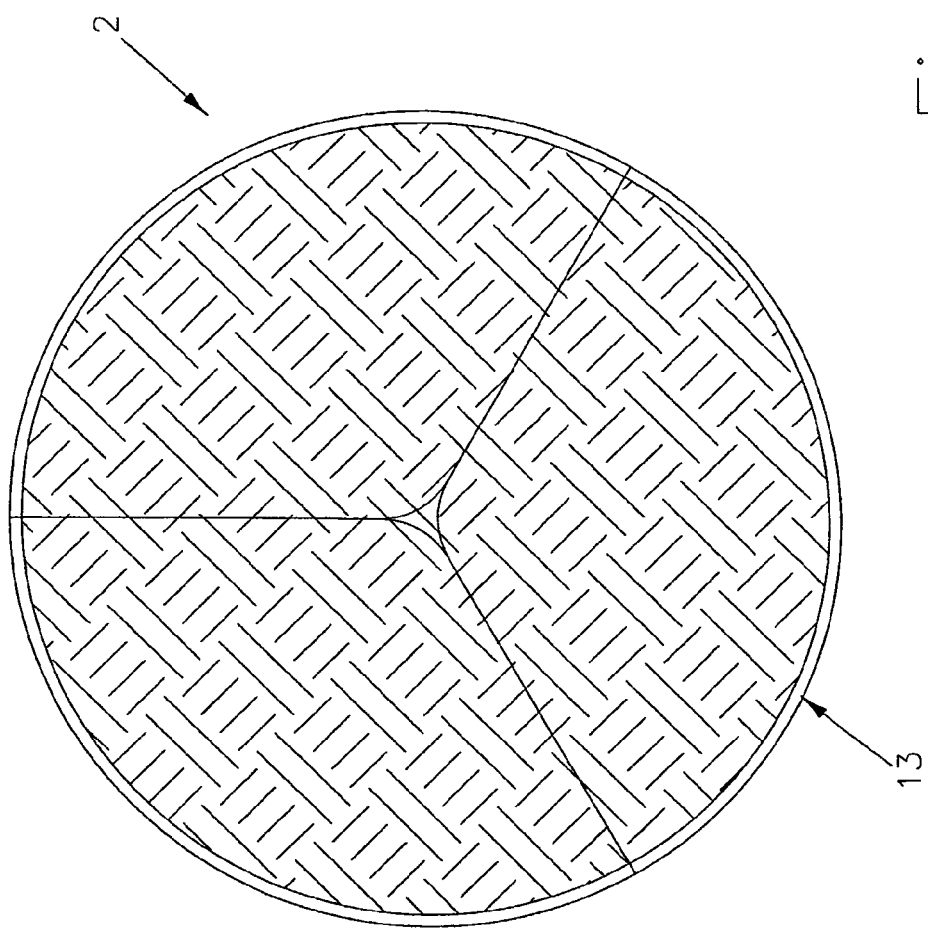
FIG. 2 is a view of the valve of FIG. 1 from below.

Referring to the drawings, a tricuspid prosthetic aortic valve 2 is basically similar in construction to a tissue valve, i.e. it is a flap valve which consists of three equal size flaps 3,4,5 of substantially planar material, each flap being formed, in plan, as slightly larger than one-third of a segment of a circle. Thus, the flaps 3,4,5 can move apart to allow fluid to pass through the valve in the direction of Arrow A (FIG. 3), but the overlap of adjacent flaps closes the valve in the reverse direction.

Each flap 3,4,5 is made of a flexible openwork structure of a medically acceptable metal. As used herein, the term "medically acceptable" means a metal which is non-toxic to the body and preferably which is inert in the body, i.e. it does not provoke a "foreign body" reaction when implanted in the body. It is envisaged that the valve of the present invention would have the flaps 3,4,5 made from titanium or a medically approved titanium alloy (for example the nickel/titanium Nitenol (trademark) alloys), but other medically acceptable metals could be used.

Figure 7C:
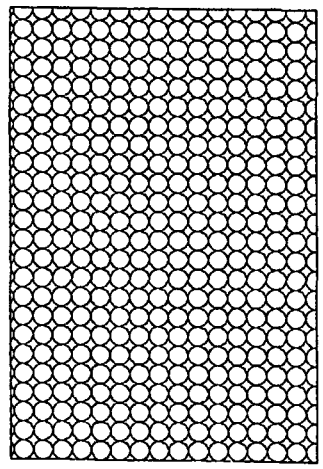
FIGS. 7 *a,b,c* and *d* show sections of knitted, woven, chainmail and perforated plate materials.
Figure 7B:
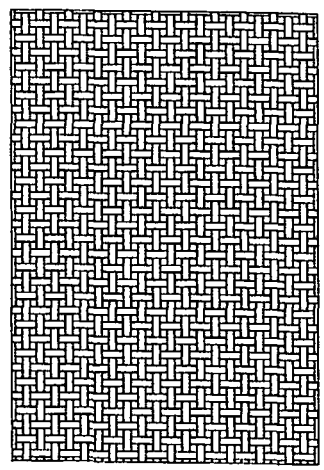
Figure 7D:
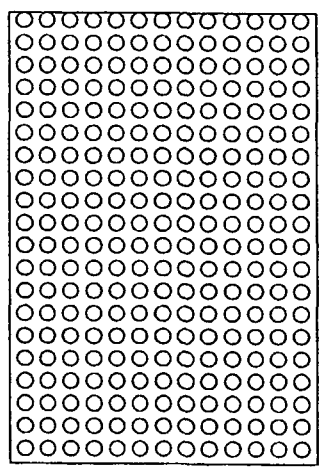
Figure 7A:
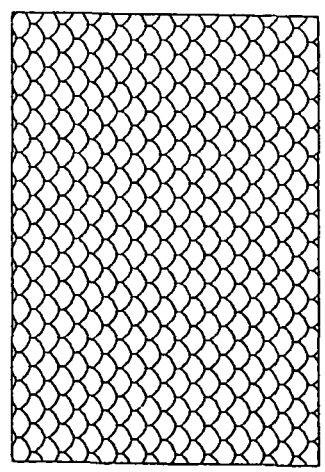

A flexible openwork structure may be made from the wire, by using a knitting type of process (FIG. 7*a*) or by manufacturing chain mail (FIG. 7*c*) (i.e. a series of separate, interlocked rings of wire); a weaving type of process (FIG. 7*b*) also may be used. Another possibility is to use a thin, flexible plate formed with multiple holes (FIG. 7*d*). The finished openwork structure must be able to flex without permanently bending.

Woven flaps or perforated plate flaps provide a relatively stiff structure, whereas the chain mail structure provides a very flexible flap; the stiffness of a knitted structure is midway between that of the woven structure and that of the chain mail structure.

Titanium and titanium alloy wires are favoured because they are known to be not only inert when implanted in the body but also to promote good tissue growth. Further, evidence from titanium implants used in other areas (e.g. the mouth) suggests that infections can be cleared from a titanium surface more easily than from other foreign materials.

Each flap 3,4,5 has a curved outer edge 3a, 4a, 5a, from each end of which a side edge 6/7, 8/9, 10/11 extends inwards to meet the adjacent side edge as an acute angle, but with the apex between the side edges curved.

As shown in FIGS. 3 and 4, the outer edges 3a, 4a, 5a of each flap are curved in the side view, with the side edges 6/7, 8/9, 10/11 raised relative to the midpoint of the outer edges. This increases the overlap between adjacent flaps where the adjacent side edges 6/8, 9/10 and 7/11 of the adjacent flaps overlap, and thus greatly reduces any risk of reverse flow through the valve (i.e. in the direction opposite to Arrow A).

The valve shown in the drawings is a semi-stented design, i.e. with a degree of reinforcing around the periphery of the valve, formed by a peripheral rib 13 which may simply be a thickened and/or reinforced area. The rib 13 is omitted from the views shown in FIGS. 3 and 4, for reasons of clarity.

The valve also may be produced as a fully stented valve, i.e. with the three flaps 3,4,5 mounted on a rigid annulus. Another possibility is to omit or reduce peripheral reinforcing altogether and produce the valve as a completely stentless valve; a stentless design (or one with a minimal stent) is advantageous for percutaneous insertion, i.e. by being inserted through the skin and then through a vein or an artery to the aorta. For percutaneous insertion, the valve has to be "scrunched" (i.e. folded in on itself) and a pronounced stent makes this impossible.

The tricuspid valve described above is the most common type of prosthetic valve, as it is in nature. However, it would be possible to form a valve in accordance with the present invention having more than three valve flaps, with the same general type of design as the tricuspid valve.

Unicuspid and bicuspid valves also are feasible; these are illustrated in FIGS. 5 and 6 respectively.

FIGS. 5a,b and c show a unicuspid valve 15 which is circular in plan and has a peripheral annular stent 16. A rigid stationary wall 17 extends outwards from the stent, perpendicular to the plane of the stent, around approximately one third of the perimeter of the stent. A single flap 18 of flexible material is U-shaped in side view, and is secured around its lower margin 19 to the edges of the stationary wall 17. The flap 18 is dimensioned such that, when the flap 18 is pushed inwards towards the stationary wall 17, the upper margin 20 of the flap can press against the wall 17, preventing fluid from passing through the valve in the direction of Arrow A. Fluid passing through the valve in the direction of Arrow B tends to push the margin 20 of the flap away from the wall 17, so that fluid can pass freely in this direction.

The flap 18 is made from a flexible openwork structure as described with reference to the flaps 3,4,5 above. The wall 17 also is made of a medically acceptable metal and may be solid or openwork.

FIGS. 6a,b and c show a bicuspid valve 20 which is circular in plan and may be produced either as a stented or a stentless valve. In the stented version, the valve has a peripheral annular stent 21, which supports a rigid wall 22 which extends outwards from the stent, perpendicular to the plane of the stent. The shape of the wall 22 may be envisaged most easily as an open ended cylinder secured along its lower edge 23 to the stent 21 and with its upper edge (i.e. the edge furthest from the stent 21) formed with two opposed U-shaped cutouts, leaving opposed sides of the wall 22 formed with a U-shaped margin 25. Along the edges of the margin 25 on each side of the wall 22, valve flaps 24, made of a flexible openwork material, are secured. Each valve flap 24 is U-shaped in side view such that its lower edge fits the margin of the cutout portion of the wall 22, and the upper edge of the flap hangs over the central portion of the valve. Thus, fluid passing on the direction of Arrow X pushes the valve flaps 24 together, closing off the valve, but fluid in the direction of Arrow Y tends to push the flaps apart and can pass freely. The wall 22 may be made of solid or openwork material.

In the stentless version, the stent 21 and wall 22 are omitted and the valve consists simply of two U-shaped valve flaps 24 arranged as an opposed pair with their upper ends 26 secured together and their curved outer margins 25a slightly stiffened to maintain the correct shape of the valve, e.g. by a peripheral wire or peripheral ribbing. The stentless version operates in the same manner as the stented version.

The valve flaps 18 and 24 in the unicuspid and bicuspid versions may be made of any of the flexible openwork structures of medically acceptable metals described with reference to the tricuspid valve.

It is envisaged that the above described valve would be implanted in a patient with an initial coating over the flaps 3,4,5 of a degradable sealing material which would prevent leakage through the openwork structure of the flaps until such time as the patient's own system had developed its own coating over the flaps, by endothelialisation.

The invention claimed is:

1. A prosthetic valve for replacing a heart valve, comprising:
   a flap valve that includes at least one moveable flap arranged to allow movement
   of liquid through the prosthetic valve only in one direction;
   the at least one flap consisting of a flexible openwork structure of a medically acceptable metal; and
   the flexible openwork structure being selected from the group consisting of: knitted wire and chainmail.

2. The prosthetic valve as claimed in
   claim 1 wherein said valve has a single flap and further includes a peripheral stent that provides a supporting wall against which said single flap is arranged to close.

3. The prosthetic valve as claimed in
   claim 1 wherein said valve includes two flaps arranged to close against each other.

4. The prosthetic valve as claimed in
   claim 3 wherein said valve further includes a peripheral stent supporting a wall extending at right angles to the plane of the stent and providing two opposed cutouts in which said flaps are mounted.

5. The prosthetic valve as claimed in claim 1 wherein said valve includes three flaps of similar size, arranged to close against each other.

6. The prosthetic valve as claimed in
   claim 5 wherein said valve also includes a peripheral rib.

7. The prosthetic valve as claimed in claim 5 wherein said valve further includes a peripheral stent upon which the three flaps are mounted.

8. The prosthetic valve as claimed in
   claim 1 wherein the medically acceptable metal is titanium or a titanium alloy.

9. A method of promoting tissue growth and endothelialisation, minimising the risk of foreign body infection following the fitting of a prosthetic valve in a living subject, said method comprising:
   providing a prosthetic valve including:
      a flap valve that includes at least one moveable flap arranged to allow movement of liquid through the prosthetic valve only in one direction;
      the at least one flap consisting of a flexible open work structure of a medically acceptable metal; and
      the flexible openwork structure being selected from the group consisting of: knitted wire and chainmail.

10. The method as claimed in claim 9 wherein the prosthetic valve is a heart valve.

11. The method as claimed in claim 9 wherein the medically acceptable metal is titanium or a titanium alloy.

12. A prosthetic valve for replacing a heart valve, comprising:
   a flap valve that includes at least one moveable flap arranged to allow movement of liquid through the prosthetic valve only in one direction;
   the at least one flap consisting of a flexible openwork structure of a medically acceptable metal coated with a degradable sealing material, the degradable sealing material being configured as an initial coating to prevent leakage through the flexible openwork structure until such time as a living subject develops a coating over the at least one flap by endothelialisation;
   and the flexible openwork structure being selected from the group consisting of: knitted wire and chainmail.

13. The prosthetic valve as claimed in claim 12 wherein said valve has a single flap and further includes a peripheral stent that provides a supporting wall against which said single flap is arranged to close.

14. The prosthetic valve as claimed in claim 12 wherein said valve includes two flaps arranged to close against each other.

15. The prosthetic valve as claimed in claim 14 wherein said valve further includes a peripheral stent supporting a wall extending at right angles to the plane of the stent and providing two opposed cutouts in which said flaps are mounted.

16. The prosthetic valve as claimed in claim 12 wherein said valve includes three flaps of similar size, arranged to close against each other.

17. The prosthetic valve as claimed in claim 16 wherein said valve also includes a peripheral rib.

18. The prosthetic valve as claimed in claim 16 wherein said valve further includes a peripheral stent upon which the three flaps are mounted.

19. The prosthetic valve as claimed in claim 12 wherein the medically acceptable metal is titanium or a titanium alloy.

20. The prosthetic valve as claimed in claim 12 wherein the prosthetic valve is a heart valve.

21. A method of promoting tissue growth and endothelialisation, minimising the risk of foreign body infection following the fitting of a prosthetic valve in a living subject, said method comprising:
   providing a prosthetic valve including:
      a flap valve that includes at least one moveable flap arranged to allow movement of liquid through the prosthetic valve only in one direction;
      the at least one flap consisting of a flexible open work structure of a medically acceptable metal coated with a degradable sealing material,
      the degradable sealing material being configured as an initial coating to prevent leakage through the flexible open work structure until such time as a living subject develops a coating over the at least one flap by endothelialisation; and
      the flexible open work structure being selected from the group consisting of: knitted wire and chainmail.

22. The method as claimed in claim 21 wherein the prosthetic valve is a heart valve.

23. The method as claimed in claim 21 wherein the medically acceptable metal is titanium or a titanium alloy.

24. A prosthetic valve for replacing a heart valve, comprising:
   a flap valve that includes at least one moveable flap arranged to open the valve in one direction of flow and close the valve in an opposite direction of flow;
   the at least one flap consisting of a flexible openwork structure of a medically acceptable metal; and
   the flexible openwork structure being selected from the group consisting of: knitted wire and chainmail.

* * * * *